Figure 1:
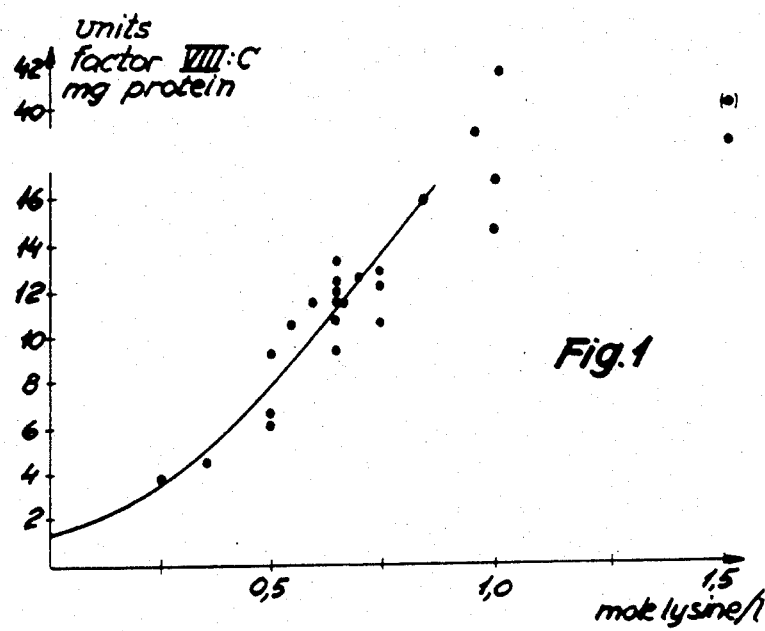

United States Patent [19]

Rasmussen et al.

[11] Patent Number: 4,650,858

[45] Date of Patent: Mar. 17, 1987

[54] CONCENTRATE OF THE ANTIHEMOPHILIC FACTOR VIII AND A PROCESS FOR PRODUCING IT

[75] Inventors: Mirella E. Rasmussen, Copenhagen; Ole Nordfang, Allerød, both of Denmark

[73] Assignee: Nordisk Gentofte A/S, Gentofte, Denmark

[21] Appl. No.: 673,753

[22] PCT Filed: Mar. 20, 1984

[86] PCT No.: PCT/DK84/00019

§ 371 Date: Oct. 30, 1984

§ 102(e) Date: Oct. 30, 1984

[87] PCT Pub. No.: WO84/03628

PCT Pub. Date: Sep. 27, 1984

[30] Foreign Application Priority Data

Mar. 21, 1983 [DK] Denmark ............................ 1274/83
May 9, 1983 [DK] Denmark ............................ 646/84
Dec. 1, 1983 [DK] Denmark ............................ 5494/83

[51] Int. Cl.$^4$ ............... A61K 35/14; A61K 35/16; C07K 3/28; C07K 5/00

[52] U.S. Cl. .................................... 530/383; 424/101; 530/384; 530/830

[58] Field of Search ................ 260/112 B; 424/107; 530/383, 384, 830

[56] References Cited

U.S. PATENT DOCUMENTS

| | | | |
|---|---|---|---|
| 3,631,018 | 12/1971 | Shanbrom et al. | 260/112 B |
| 3,652,530 | 3/1972 | Johnson et al. | 260/112 B |
| 3,682,881 | 8/1972 | Fekete et al. | 260/112 B |
| 4,027,013 | 5/1977 | Bick et al. | 260/112 B X |
| 4,069,216 | 1/1978 | Shanbrom | 260/112 B |
| 4,093,608 | 6/1978 | Iga et al. | 260/112 B |
| 4,289,691 | 9/1981 | Rock et al. | 260/112 B |
| 4,297,344 | 10/1981 | Schwinn et al. | 424/101 |
| 4,348,315 | 9/1982 | Blombäck et al. | 260/112 B |
| 4,361,509 | 11/1982 | Zimmerman et al. | 260/112 B |
| 4,387,092 | 6/1983 | Liautaud et al. | 424/101 |
| 4,404,131 | 9/1983 | Schwarz et al. | 260/112 B |
| 4,435,318 | 3/1984 | Pabst et al. | 260/112 B |
| 4,446,134 | 5/1984 | Naito et al. | 424/101 |
| 4,455,301 | 6/1984 | Mitra et al. | 424/101 |
| 4,465,574 | 8/1984 | Mattock et al. | 424/101 X |
| 4,478,825 | 10/1984 | Bloom | 424/101 |
| 4,486,410 | 12/1984 | Fisher | 424/101 |
| 4,495,175 | 1/1985 | Chavin et al. | 424/101 |
| 4,508,709 | 4/1985 | Amphlett et al. | 424/101 |
| 4,543,210 | 9/1985 | Mitra et al. | 424/101 X |

FOREIGN PATENT DOCUMENTS

| | | |
|---|---|---|
| 0018561 | 11/1980 | European Pat. Off. |
| 0032655 | 7/1981 | European Pat. Off. |
| 2715832 | 10/1977 | Fed. Rep. of Germany |
| 2460305 | 1/1981 | France |
| 2083047 | 3/1982 | United Kingdom |

OTHER PUBLICATIONS

Am. J. Med. Sciences, 250, pp. 643–651 (1965), Webster et al.
Brit. J. Haematology, 21, 1–20 (1971), Newman et al.
Jama, 205, No. 9, 613–617 (1968), Brinkhous et al.
Rote Liste, 1978, Bundesverband, Preparation No. 47024.

*Primary Examiner*—Howard E. Schain
*Attorney, Agent, or Firm*—Ladas & Parry

[57] ABSTRACT

Production of a high purity concentrate of the antihemophilic Factor VIII (AHF) by precipitation of an aqueous solution of cryoprecipitate from blood plasma in a first step with such an amount of polyethylene glycol (PEG), preferably about 4% by weight, as will precipitate a substantial amount of the present fibrinogen, subjecting the fibrinogen-free solution to a second precipitation step with preferably about 12% by weight of PEG in the presence of a salting-in agent, such as an amino acid, in particular lysine or arginine, or a carbohydrate, and then recovering the precipitate with a concentrated content of the present Factor VIII. The obtained Factor VIII concentrate with a very low content of immunoglobulins and other plasma proteins has a solubility in an aqueous injection medium of 45 to 500 units/ml and a high specific activity of up to 50 units/mg protein.

14 Claims, 2 Drawing Figures

CONCENTRATE OF THE ANTIHEMOPHILIC FACTOR VIII AND A PROCESS FOR PRODUCING IT

The present invention relates to a concentrate of the antihemophilic Factor VIII, called AHF, and a process for producing such a concentrate.

It is known that the ability of the blood to coagualate is controlled by a system of coagulation proteins, of which AHF or Factor VIII is an important component.

Hemophilia A patients have completely or partly lost the ability to produce AHF. AHF-containing preparations are injected to treat this disease, and it is therefore important to have preparations containing suitably high concentrations of AHF and with as low a content of other proteins as possible, such as fibrinogen and immunoglobulins.

In particular in the treatment of inhibitor patients—i.e. patients who produce antibodies against AHF and who therefore need administration of the preparation in excess—with high doses of AHF, it is important that the specific activity (units AHF/mg protein) is high since supply of "other proteins" in large amounts may cause undesirable side effects. Side effects in AHF treatment caused by immunoglobulins is described e.g. by Tilsner et al., Münch. Med. Wschr. 124 (1982) No. 22, p. 553–557.

AHF is normally recovered from the so-called cryoprecipitate, which mainly consists of fibrinogen, albumin, IgG and IgM, while AHF constitutes less than 1% of the total protein amount. The specific activity of a cryoprecipitate is typically 0.1 to 0.3 unit AHF/mg protein.

It is known that part of the unnecessary protein can be removed by precipitation with glycine or polyethylene glycol (PEG). Precipitation can optionally be accomplished several times, first with one precipitant and then with the other.

Thus, it has been kown for a long time to precipitate AHF with about 2M glycine at a low temperature, cf. Webster et al., Amer. J. Med. Sc. 250, No. 6, p. 643–650 (1965). Webster used a cryoprecipitate which was dissolved in water and fractionated at a low temperature (<10° C.) with increasing concentrations of glycine until 2.3 molar. This type of precipitation relies upon the fact that AHF is precipitated in the cold together with fibrinogen by addition of glycine. This results in a specific activity of 0.3 to 0.5 unit AHF/mg protein.

It is known from the EP Patent Specification No. 32,655, cf. the DK Patent Application No. 1762/80, that when redissolved cryoprecipitate is fractionated with 2M glycine as a precipitant at higher temperatures such as 30° to 45° C., a large proportion of the other proteins, such as fibrinogen, is precipitated first so that AHF remains in the supernatant from which it can be recovered.

When PEG is used as a precipitant, fractionated PEG precipitation is frequently accomplished where most of the fibrinogen and some IgM are removed by precipitation with a low PEG concentration (2 to 6%), and then AHF is precipitated from the albumin-containing supernatant with a high PEG concentration (5 to 15%). Such PEG/PEG precipitations are described by e.g. Newman et al., Brit. J. Haematology 21, 1971, p. 1; the U.S. Pat. No. 3,652,530; the DK Patent Application No. 364/77; the FR Patent Specification No. 2,460,305; the DK Patent Application No. 3602/81. These methods provide an AHF concentrate with a specific activity of 1 to 3 units/mg protein.

Processes comprising multi-step precipitations where more than one precipitant is used are likewise known. Glycine precipitation at a low temperature, e.g., can be carried out before or after PEG/PEG precipitations, and glycine precipitations can optionally be carried out both before and after the PEG/PEG precipitations. This is described in the U.S. Pat. No. 3,682,881 and the U.S. Pat. No. 3,631,018. Generally, this results in preparations with a specific activity of 1 to 3 units/mg protein.

When in this context precipitation with glycine is accomplished at a low temperature, the AHF-containing precipitate is utilized, i.e. in subsequent PEG precipitations on a redissolved AHF-containing precipitate there is only a low concentration of glycine in the solution.

If glycine is used at a high temperature in connection with PEG precipitation, glycine precipitation is first accomplished leaving AHF in the supernatant where the concentration of glycine is high, and AHF is then precipitated from the supernatant by PEG precipitation at a high PEG concentration. This can give a specific activity of 1 to 3 units/mg protein.

The concentrate obtained by this glycine/PEG precipitation type resembles a concentrate obtained by PEG/PEG precipitation. As appears from table 1, the 1st precipitation supernatant contains more IgM and IgG after a warm precipitation with 2M glycine than after a precipitation with a low PEG concentration (4%). After the final precipitation with a high PEG concentration (9%) the concentrate from the glycine/PEG precipitation contains less IgM and IgG than the concentrate from the PEG/PEG precipitation.

TABLE 1

Comparison between PEG/PEG and warm glycine/PEG precipitation of AHF from cryoprecipitate

| Fraction | % AHF | % IgM | % IgG |
|---|---|---|---|
| Cryoprecipitate | 100 | 100 | 100 |
| 1st PEG supernatant | 72 | 38 | 55 |
| PEG/PEG concentrate | 40 | 24 | 15 |
| Glycine supernatant | 68 | 76 | 79 |
| Glycine/PEG concentrate | 36 | 18 | 8 |

The reason of this is not known, but it must be assumed that the polar amino acid in the glycine supernatant has a salting-in effect, in particular on basic proteins, so that IgM and IgG do not readily precipitate with PEG. The concentrate obtained by the glycine/PEG precipitation, however, still has an undesirably high content of fibrinogen, IgG and IgM, cf. table 2 below.

The object of the present invention is to provide a high purity AHF preparation with a previously unattainable solubility and a high specific activity.

The invention is based on the surprising finding that a particularly pure AHF preparation, essentially freed of other proteins, in particular immunoglobulins, can be obtained by fractionating a cryoprecipitate with PEG in such a manner that a substantial amount, preferably at least 80%, of the fibrinogen is first precipitated, and then accomplishing precipitation in a subsequent step with more PEG in the presence of a salting-in agent. The addition of the salting-in agent per se does not cause any precipitations, but the presence of the salting-in agent modifies the conditions under the subsequent PEG precipitation so that a sharper fractionation, i.e. a purer AHF preparation with a high specific activity, is obtained, cfr. the following table 2. The high purity permits the preparation to be redissolved in a very small volume of aqueous injection medium in a concentration of 45 to 500, frequently 200 to 500 units of Factor VIII:C (AHF) per ml. As a normal injection dose is 1000 units, an injection preparation of about 2 to 5 ml will thus suffice. As the solubility of the best commercially available AHF preparations is stated to be 40 to 50 units per ml corresponding to an injection volume of 25 to 20 ml, the preparation of the invention thus involves a very significant relief for the patient.

TABLE 2

Effect of glycine addition under PEG/PEG precipitation from redissolved cryoprecipitate

| Process | AHF units/mg | % IgG | % IgM | % Fibr. |
|---|---|---|---|---|
| Cryoprecipitate | 0.32 | 100 | 100 | 100 |
| 4% PEG/9% PEG | 2.53 | 15 | 24 | 1 |
| 2 M glycine/9% PEG | 2.27 | 8 | 18 | 2 |
| 4% PEG/2 M glycine + 12% PEG | 4.36 | 4 | 13 | 0.5 |

Thus, in the precipitation according to the invention, glycine is used as a salting-in agent as it stabilizes the undesired proteins by keeping them in solution, whereas the previously known methods rely on the salting-out effect of glycine on fibrinogen/AHF. So, the use of a salting-in agent under a PEG/PEG precipitation provides a more selective precipitation of AHF.

Without being tied down to any specific theory, it is assumed that the effect of the salting-in agent is due to its increasing the difference in surface charge between Factor VIII and the other proteins, in particular IgG.

It is important to remove most of the fibrinogen in the first step because, otherwise, the AHF preparation would be highly contaminated with fibrinogen, and because the presence of fibrinogen in the second step would counteract the salting-in effect and prevent selective precipitation of Factor VIII.

The salting-in agent may appropriately be an amino acid, in particular basic amino acids such as lysine, arginine and histidine, as well as polar amino acids such as serine, glutamine and glycine. Examples of other suitable salting-in agents are $\epsilon$-aminohexanoic acid and carbohydrates such as mono-, di- and oligosaccharides, as well as sugar alcohols, e.g. glucose, saccharose, sorbitol and glycerol.

A survey is given in table 3.

TABLE 3

Effect of salting-in agents on PEG/PEG precipitation of AHF from redissolved cryoprecipitate

| Salting-in agent | Spec. activity units/mg | % yield of AHF from plasma |
|---|---|---|
| None | 2.53 | 18 |
| 2 M glycine | 4.36 | 17 |
| 0.5 M serine | 2.94 | 19 |
| 0.5 M glutamic acid | 1.28 | 17 |
| 0.5 M lysine | 8.4 | 18 |
| 0.5 M arginine | 7.0 | 14 |
| 1.0 M $\epsilon$-aminohexanoic acid | 5.0 | 10 |
| 1.5 M glucose | 3.85 | 18 |
| 1.0 M saccharose | 5.35 | 20 |

The preferred salting-in agent is lysine. The drawing shows the influence of lysine on PEG/PEG precipitation of AHF, expressed as units AHF/mg protein (FIG. 1) and % yield, respectively, in relation to the cryoprecipitate at different lysine concentrations (FIG. 2). Lysine is preferably added in concentrations of 0.1 to 0.9, in particular 0.4 to 0.8, most preferably 0.5 to 0.7 mole/l.

Figure 2:
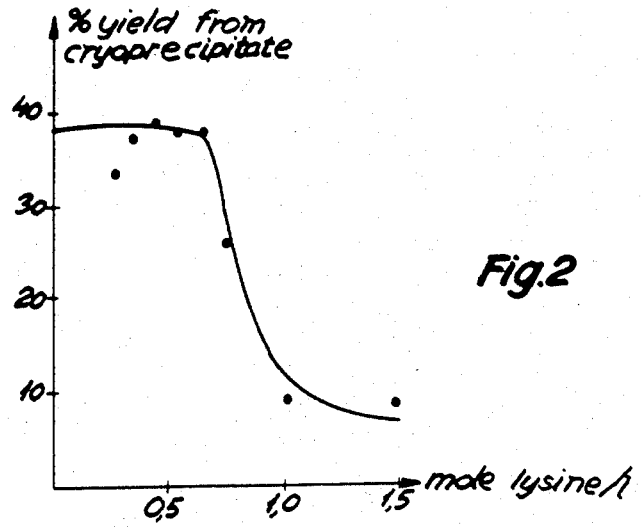

As appears from FIG. 1, there is proportionality between added amount of lysine and specific activity of the end product, but even small lysine amounts have a distinct effect. As appears from FIG. 2, the yield of AHF, however, declines at the PEG concentration used if more than 0.75M lysine is employed, as this amount of lysine has also a salting-in effect on AHF.

Another preferred salting-in agent is arginine, whose influence on the PEG/PEG precipitation of AHF appears from table 4 below, from which it will be seen that satisfactory yields are obtained at concentrations of 0.2 to 0.8. In view of the yield the preferred amount is 0.3 to 0.5, in particular 0.4 mole/l.

TABLE 4

Influence of arginine on PEG/PEG precipitation of AHF

| Mole arginine/l | % yield from plasma | units AHF/mg protein |
|---|---|---|
| 0 | 20 | 2.3 |
| 0.2 | 20 | 4.9 |
| 0.4 | 17 | 6.4 |
| 0.6 | 14 | 6.1 |
| 0.8 | 4 | 4.6 |

The employed concentrations of PEG and salting-in agent as well as pH during precipitation depend in particular upon the salting-in agent used as it can be said generally that salting-agents of greater charge can be used in smaller concentrations. The selected concentration of the salting-in agent is based on a compromise since high concentrations can reduce the IgG amount almost completely, but some Factor VIII is salted in at the same time, which reduces the yield.

PEG with a molecular weight of 200 to 20,000, preferably 2,000 to 12,000, in particular 3,000 to 6,000, can be used, but PEG 3,000 is preferred. The PEG concentration in the first precipitation step is usually 2 to 6% by weight, preferably about 4% by weight, and is usually 6 to 20% by weight in the second step, preferably about 12% by weight: pH in the first precipitation step may be 6.0 to 8.5, preferably 6.2 to 6.6, in particular about 6.4, and in the second step 5.0 to 8.5, preferably 6.0 to 6.6, in particular about 6.3.

The temperature in the first precipitation step may be 6° to 20° C., preferably 18° to 22° C. In the second precipitation step the temperature is also preferably 18° to 22° C. (room temperature).

In the recovery of the present Factor VIII concentrate cryoprecipitate from human blood plasma or other Factor VIII-containing blood fractions may be used, just as plasma fractions from other species of animals, e.g. pigs, may be used. In this case, a blood fraction obtained e.g. by PEG precipitation is normally used instead of the cryoprecipitate.

The process of the invention will be explained more fully below by means of some examples, which also illustrate the processing of the concentrate. To produce the preparation, the AHF solution may if desired be subjected to a heat treatment for 10 hours at 60° C. in the presence of a suitable stabilizer so as to provide a safeguard against hepatitis.

EXAMPLE 1

Cryoprecipitate from 600 ml of human blood plasma is redissolved in 28 ml of citrate/glucose buffer and is freed of prothrombin complex by adsorption with Al$_2$O$_3$. Then 4% by weight of PEG 3,000 is added. pH is adjusted to 6.4 with 0.5M HCl, and the mixture is incubated for 30 minutes at room temperature. Precipitated protein is removed by centrifugation, and lysine-HCl is added until a concentration of 0.55 mole/l. An additional 8% by weight of PEG 3,000 is added, and pH is adjusted to 6.3 with 0.1M NaOH. After incubation for 45 minutes at room temperature the precipitate is isolated by centrifugation and is redissolved in citrate/glucose-NaCl, pH 7.8. The redissolved precipitate has a specific activity of 12 units Factor VIII:C (AHF) per mg protein, and the yield of Factor VIII:C from plasma is 20%.

The following table 5 shows that the specific activity can be significantly increased and the content of immunoglobulin G can be reduced in relation to a PEG/PEG precipitation without the presence of a salting-in agent.

EXAMPLE 2

To 30 ml of cryo-solution, adsorbed with Al$_2$O$_3$, is added 4% by weight of PEG 3,000. pH is adjusted to 6.4 with 0.5M HCl, and the mixture is incubated for 30 minutes at room temperature. Precipitated protein is removed by centrifugation, and "salting-in agent" is added. Then an additional 8% by weight of PEG 3,000 is added, and pH is adjusted to 6.3 with 0.1M NaOH. After incubation for 45 minutes at room temperature the precipitate is isolated by centrifugation and is redissolved in citrate/glucose NaCl, pH 7.8.

Table 6 gives the results obtained for the various salting-in agents.

TABLE 5

| n = 3 Process | Units Factor VIII:C in end product | mg protein in end product* | thereof IgG mg | % Factor VIII:C from plasma | Specific activity units/ mg protein |
|---|---|---|---|---|---|
| 4% PEG - 8½% PEG | 109 | 38 | 10 | 19 | 2.86 |
| 4% PEG - 12% PEG | 104 | 74 | 30 | 18 | 1.40 |
| 4% PEG - 12/ PEG with 0.55 M lysine | 112 | 9 | 0.3 | 20 | 12.44 |

*determined at OD$^{290}$, E$^{1\%}_{280}$ = 10

TABLE 6

| Salting-in agent mole/l | Units Factor VIII:C in end product | mg protein in end product* | thereof IgG mg | % Factor VIII:C from plasma | Specific activity units/ mg protein |
|---|---|---|---|---|---|
| none | 108 | 108 | 24 | 19 | 1.0 |
| 2 M glycine | 102 | 21 | 2 | 18 | 4.9 |
| 1.5 M lysine | 51 | 2.5 | 1 | 9 | 20.0 |
| 1.0 M ε-amino-hexanoic acid | 60 | 20 | 1 | 11 | 3.0 |
| 1.5 M glucose | 108 | 49 | 7 | 19 | 2.2 |
| 1.0 M saccharose | 123 | 29 | 5 | 22 | 4.2 |
| 0.35 M arginine | 108 | 17 |  | 19 | 6.4 |

EXAMPLE 3

Cryoprecipitate from 2.5 l of plasma is redissolved in 100 ml of citrate/glucose buffer and freed of prothrombin complex by adsorption with Al$_2$O$_3$. 4% by weight of PEG 3,000 is added. pH is adjusted to 6.4 with 0.5M HCl, and the mixture is incubated for 30 minutes at room temperature. Precipitated protein is removed by centrifugation, and arginine-HCl is added until a concentration of 0.40 mole/l. An additional 8% by weight of PEG 3,000 is added, and pH is adjusted to 6.3 with 0.1M NaOH. After incubation for 45 minutes at room temperature the precipitate is isolated by centrifugation and is redissolved in 20 ml of citrate/saccharose/NaCl, pH 7.8. The concentrate contains 360 units Factor VIII:C and 52 mg protein (specific activity 7 units/mg).

EXAMPLE 4

Cryoprecipitate from 2.5 l of plasma is redissolved in 100 ml of citrate/glucose buffer and freed of prothrombin complex by adsorption with Al$_2$O$_3$. 4% by weight of PEG 3,000 is added. pH is adjusted to 6.4 with 0.5M HCl, and the mixture is incubated for 30 minutes at room temperature. Precipitated protein is removed by centrifugation, and lysine-HCl is added until a concentration of 0.55 mole/l. An additional 8% by weight of PEG 3,000 is added, and pH is adjusted to 6.3 with 0.1M NaOH. After incubation for 45 minutes at room temperature the precipitate is isolated by centrifugation and is redissolved in 5 ml of citrate/saccharose/NaCl, pH 7.8. The concentrate contains 460 units Factor VIII:C and 30 mg protein (specific activity 15 units/mg).

EXAMPLE 5

Cryoprecipitate from 80 kg of plasma is redissolved in 2500 ml of citrate buffer and freed of prothrombin complex by adsorption with Al$_2$O$_3$. 4% by weight of PEG 3,000 is added. pH is adjusted to 6.4 with 0.5M HCl, and the mixture is incubated for 30 minutes at room temperature. Precipitated protein is removed by centrifugation, and lysine-HCl is added until a concentration of 0.55 mole/l. An additional 8% by weight of PEG 3,000 is added, and pH is adjusted to 6.3 with 0.1M NaOH. After incubation for 45 minutes at room temperature the precipitate is isolated by centrifugation and is redissolved in 60 ml of citrate/saccharose/NaCl. The solution is sterile-filtrated and dispensed into 15 vials. After freezing and freeze-drying each vial contains 1000 units of AHF, with a specific activity of 37 units/mg protein.

It is evident to a skilled person that salting-in agent effect on a PEG/PEG precipitation can be obtained under other conditions than those stated in the foregoing. Thus, at a different pH and temperature other concentrations of PEG and salting-in agent are to be used. The most expedient conditions can be determined by experiments.

What is claimed is:

1. A process for producing an AHF concentrate substantially free of denatured AHF and immunoglobulins and having a solubility in an aqueous injection medium of from 200 to 500 units AHF/ml and a specific activity of from 3.85 to 50 units AHF/mg protein which comprises subjecting a solution of a cryoprecipitate from blood plasma to the following treatment steps:
   (a) removal of prothrombin present,
   (b) a first treatment with from 2 to 6% by weight of PEG 200–20,000 thereby to precipitate a substantial amount of the fibrinogen present,
   (c) a second treatment of the supernatant from the first PEG precipitation with from 6 to 20% by weight of PEG 200 to 20,000 in the presence of an effective amount of a salting-in agent selected from the group consisting of amino acids, carbohydrates and sugar alcohols thereby to precipitate the AHF while essentially keeping the other proteins present in solution,
   (d) recovering the precipitate having a concentrated content of AHF.

2. A process according to claim 1, wherein the salting-in agent used in the second precipitation step is a basic amino acid.

3. A process according to claim 2, wherein the salting-in agent is lysine or arginine.

4. A process according to claim 1, wherein the salting-in agent used in the second precipitation step is a carbohydrate selected from mono- and disaccharides.

5. A process according to claim 4, wherein the salting-in agent is saccharose.

6. A process according to claim 4, wherein PEG is added in the first precipitation step until a concentration of about 4% by weight of the solution.

7. A process according to claim 4, wherein PEG is added in the second precipitation step corresponding to a total concentration of about 12% by weight.

8. A process according to claim 3, wherein lysine or arginine is added in the second precipitation step in an amount corresponding to a concentration of 0.1 to 0.9 mole/l.

9. A process according to claim 8, wherein the pH in the first precipitation step is 6.0 to 8.5 and in the second precipitation step is 5.0 to 8.5.

10. A process according to claim 9, wherein the recovered Factor VIII concentrate is heated to 60° C. for at least 10 hours in the presence of a suitable stabilizer so as to provide a safeguard against hepatitis.

11. A process according to claim 10, wherein the recovered Factor VIII concentrate is freeze-dried.

12. A process according to claim 8, wherein lysine or arginine is added in an amount corresponding to 0.3 to 0.8 mole/l.

13. A process according to claim 9, wherein the pH in the first precipitation step is 6.2 to 6.6 and in the second precipitation step is 6.0 to 6.6.

14. A process according to claim 13, wherein the pH in the first precipitation step is about 6.4 and in the second precipitation step is about 6.3.

* * * * *